United States Patent
Shin et al.

(10) Patent No.: US 8,563,564 B2
(45) Date of Patent: *Oct. 22, 2013

(54) COMPOSITION FOR SKIN EXTERNAL APPLICATION CONTAINING GALLOCATECHIN GALLATE FOR MOISTURIZING EFFECT ON THE SKIN

(75) Inventors: Hyun Jung Shin, Anyang-si (KR); Jeong Ki Kim, Yongin-si (KR); Su Nam Kim, Gangneung-si (KR); Sang Min Lee, Yongin-si (KR); Byeong Gon Lee, Suwon-si (KR); Ih Seop Chang, Yongin-si (KR)

(73) Assignee: Amorepacific Corporation, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 13/067,719

(22) Filed: Jun. 22, 2011

(65) Prior Publication Data

US 2012/0010226 A1 Jan. 12, 2012

Related U.S. Application Data

(62) Division of application No. 12/064,997, filed as application No. PCT/KR2006/003579 on Sep. 8, 2006, now abandoned.

(30) Foreign Application Priority Data

Sep. 16, 2005 (KR) .................... 10-2005-0086821

(51) Int. Cl.
*A01N 43/90* (2006.01)
*A61K 31/522* (2006.01)

(52) U.S. Cl.
USPC .................................. 514/263.34

(58) Field of Classification Search
USPC .................................. 514/236.34
See application file for complete search history.

(56) References Cited

U.S. PATENT DOCUMENTS

| 5,665,367 | A  | 9/1997  | Burger et al. |
| 6,861,062 | B2 | 3/2005  | Silva et al. |
| 2002/0106388 | A1 | 8/2002  | Pugliese |
| 2003/0211184 | A1 | 11/2003 | Hoving et al. |
| 2004/0161435 | A1 | 8/2004  | Gupta |
| 2005/0003024 | A1 | 1/2005  | Oblong et al. |
| 2005/0031737 | A1 | 2/2005  | Lines et al. |

FOREIGN PATENT DOCUMENTS

| JP | 07-258066 | 10/1995 |
| JP | 2001-502685 | 2/2001 |
| JP | 2001-097968 | 4/2001 |
| JP | 2002-069496 | 3/2002 |
| JP | 2004-537575 | 12/2004 |
| WO | WO 2004/014413 | 2/2004 |

OTHER PUBLICATIONS

Sugita-Konishi (Biochimica et Biophysica Acta 1472 (1999) 42-50).*
International Search Report for PCT/KR2006/003579 dated Dec. 11, 2006.
English translation of Mar. 6, 2012 Office Action in JP 2008-531009.
English translation of Feb. 19, 2013 Office Action in JP 2008-531009.
Fragrance Journal, Japan, Fragrance Journal Ltd., Apr. 15, 2000, vol. 28, No. 4, pp. 66-73.

* cited by examiner

*Primary Examiner* — Shirley V Gembeh
(74) *Attorney, Agent, or Firm* — Nixon & Vanderhye P.C.

(57) ABSTRACT

The present invention relates to a composition for external skin application having a skin-moisturizing effect, which comprises gallocatechin gallate as an active ingredient. More particularly, the composition for external skin application comprises gallocatechin gallate as an active ingredient to activate peroxisome proliferator activated receptor isoform alpha (PPAR-α), to stimulate expression of filaggrin and involucrin that are skin-moisturizing factors, and thus to provide excellent anti-drying and skin-moisturizing effects. More particularly, the composition for external skin application may further comprise theobromine and quercetin in addition to gallocatechin gallate to maximize such effects.

8 Claims, 4 Drawing Sheets

[Comp. Example 2]   [Example 6]   [Example 7]

COMPOSITION FOR SKIN EXTERNAL APPLICATION CONTAINING GALLOCATECHIN GALLATE FOR MOISTURIZING EFFECT ON THE SKIN

This application is a divisional of U.S. application Ser. No. 12/064,997 filed Aug. 11, 2008 now abandoned, which in turn is the US national phase of International Application No. PCT/KR2006/003579 filed Sep. 8, 2006 which designated the US and claims priority to Korean Application No. 10-2005-0086821 filed Sep. 16, 2005, the entire contents of each of which are hereby incorporated by reference.

TECHNICAL FIELD

The present invention relates to a composition for external skin application having a skin-moisturizing effect, which comprises gallocatechin gallate as an active ingredient. More particularly, the composition for external skin application according to the present invention comprises gallocatechin gallate as an active ingredient to activate peroxisome proliferator activated receptor isoform alpha (PPAR-α), to stimulate expression of filaggrin and involucrin that are skin-moisturizing factors, and thus to provide excellent anti-drying and skin-moisturizing effects. More particularly, the composition for external skin application according to the present invention may further comprise theobromine and quercetin in addition to gallocatechin gallate to maximize such effects.

BACKGROUND ART

In general, the skin is divided into the epidermis, the dermis and the subcutaneous tissue when viewed from the exterior, and functions to protect the whole organs in the body from variations in temperature and humidity, ultraviolet rays, and other external physical and chemical environmental irritations. Particularly, the epidermis has an important role in preventing evaporation of moisture in the human body.

The epidermis is divided into the stratum corneum, the stratum granulosum, the stratum spino and the stratum basale. Additionally, keratinocytes present in the stratum corneum serve as bricks and intercellular lipids present between keratinocytes serve as mortar, thereby forming skin barriers (J. Invest. Dermatol. 80 (Suppl.) 44-49, 1983). Further, a high concentration of natural moisturizing factors (NMF) is present in keratinocytes of healthy humans so that the skin retains moisture. For example, amino acids, which are water soluble materials, are effectively bound to moisture, thereby inhibiting moisture from drying on the skin (J. Invest. Dermatol., 54, 24-31, 1970).

However, skin drying and roughening phenomena, caused by a drop in moisture content of the stratum corneum and including loose, dry and inanimate skin conditions, occur due to various causes. Such causes include artificial temperature control for cooling/warming an indoor space depending on variations in the living environment and pattern, diverse stresses generated from social activities and skin stresses caused by environmental pollution, frequent face-washing depending on makeup habits, and natural skin aging. Therefore, there has been an increasing need for a skin moisturizing agent.

According to the prior art, a humectant capable of absorbing moisture or an occlusive moisturizer capable of preventing moisture evaporation have been used as moisturizing agents so as to increase moisture retainment in the stratum corneum. Such humectants include glycerin, propylene glycol, 1.3-butylene glycol, polyethylene glycol, sorbitol, sodium 2-pyrrolidone-5-carboxylate, or the like. However, such humectants have a disadvantage in that they have a highly sticky and dense feel when applied on the skin. Additionally, as the occlusive moisturizers, lipids such as ceramides or essential fatty acids and lipid complexes have been used (J. Invest. Dermatol. (5), 731-740, 1994). However, such occlusive moisturizers have difficulty in maintaining stability of an emulsified formulation and are not amenable to production of transparent gel-like cosmetic products.

Meanwhile, peroxisome proliferator activated receptors (PPAR) are known nuclear hormone receptors having the three isoforms of α, β/δ and γ distributed over various tissues. Peroxisome proliferator activated receptor isoform α (also referred to as 'PPAR-α') has been identified first based on the mechanism of controlling genes encoding fatty acid oxidase by the reaction with a peroxisome proliferator factor such as a fibric acid derivative (Issemann and Green, Nature, 1990, 347: 645-650). Additionally, it is disclosed that fatty acids play an important role in tissues expressed by PPAR-α (Leone et al., Proc. Natl. Acad. Sci. USA, 1999, 96: 7473-7478). Lipid activators of PPAR-α, such as linoleic acid, etc., are known to those skilled in the art. It is demonstrated that such activators enhance formation of an epithelial barrier in vitro (Hanley et. al., J. Clin. Inv., 1977, 100: 705-712). However, in the relevant art, there is no disclosure of a skin cosmetic agent utilizing a mechanism of controlling PPAR activities other than a cosmetic composition (WO01/008653) for preventing and treating skin aging.

DISCLOSURE

Technical Problem

Accordingly, the present invention has been made to solve the above-mentioned problems occurring in the prior art. The inventors of the present invention have many studies to search for the components that shows a skin-moisturizing effect by controlling activity of the peroxisome proliferator activated receptor isoform alpha (PPAR-α), among various factors affecting the skin in terms of skin moisturization and skin protection. Then, we have found that when a composition for external skin application comprises gallocatechin gallate contained in green tea leaves, it activates the peroxisome proliferator activated receptor isoform alpha (PPAR-α) and stimulates expression of skin moisturizing factors such as filaggrin and involucrin, and thus provides excellent skin moisturizing and anti-drying effects. Particularly, we have also found that when the composition further comprises theobromine and quercetin, besides gallocatechin galate, at an optimized ratio, the above effects can be maximized. The present invention is based on these findings.

Therefore, it is an object of the present invention to provide a composition for external skin application having a skin-moisturizing effect, which comprises gallocatechin gallate as an active ingredient.

It is another object of the present invention to provide a composition for external skin application having a skin-moisturizing effect, which further comprises theobromine and quercetin at an optimized ratio in addition to the above composition comprising gallocatechin gallate.

Technical Solution

According to an aspect of the present invention, the composition for external skin application having a skin-moisturizing effect comprises gallocatechin gallate as an active ingredient. According to another aspect of the present invention, the composition further comprises theobromine and quercetin at an optimized ratio.

DESCRIPTION OF DRAWINGS

Further objects and advantages of the invention can be more fully understood from the following detailed description taken in conjunction with the accompanying drawings, in which.

BEST MODE

Hereinafter, the present invention will be explained in more detail.

The composition for external skin application having a skin-moisturizing effect according to the present invention comprises gallocatechin gallate as an active ingredient to activate the peroxisome proliferator activated receptor isoform alpha (PPAR-α) and to provide excellent skin-moisturizing and anti-drying effects.

Additionally, the composition for external skin application having a skin-moisturizing effect may further comprise theobromine and quercetin contained in green tea leaves as active ingredients, in addition to gallocatechin gallate.

In the composition for external skin application having a skin-moisturizing effect according to the present invention, each active ingredient is present in an amount of 0.001~30 wt % based on the total weight of the composition.

One of the known methods for determining PPAR activation by observing PPAR activation/inactivation is reporter gene assay (Kliewer et. al., Nature, 1992, 358: 771-774). The reporter gene assay includes cloning a base sequence containing a promoter of interest and reporter genes, and injecting the base sequence into eukaryotic cells to activate transcription and to control the expression of a protein. Herein, protein expression increases as the promoter is activated. The reporter gene used for the first time is CAT (chloramphenicol acetyltransferase) gene. Recently, luciferase gene has been used widely. In the present invention, a Dual-Luciferase Reporter Assay System Kit available from Promega Co. was used.

Meanwhile, when the composition for external skin application having a skin-moisturizing effect according to the present invention further comprises theobromine and quercetin contained in green tea leaves as active ingredients, in addition to gallocatechin gallate, at an optimized ratio, it can provide a higher skin-moisturizing effect by activating the peroxisome proliferator activated receptor isoform alpha (PPAR-α).

In the composition for external skin application according to the present invention, gallocatechin gallate, theobromine and quercetin are used at an optimized ratio as follows: at least 0.4 moles of theobromine and at least 0.4 moles of quercetin in combination with 0.7 moles or less of gallocatechin gallate (GCG); at least 0.3 moles of theobromine and at least 0.3 moles of quercetin in combination with 0.7~1.4 moles of gallocatechin gallate (GCG); and at least 0.2 moles of theobromine and at least 0.2 moles of quercetin in combination with 1.4 moles or more of gallocatechin gallate (GCG).

When analyzing functions of various components contained in green tea leaves, an integrated experimental and analytical process is required to obtain the greatest information under a given estimated cost in a predetermined time. For this purpose, DOE (Design of Experiments) has been used. DOE is a methodology for designing, performing and stastically analyzing a science study. Particularly, according to DOE, a series of experimental steps is designed and carried out, wherein levels of a controllable input value are gradually varied in order to determine the cause of variance in an output value of a specific step. By doing so, it is possible to construct an experimental strategy for determining experimental conditions under which the greatest information can be obtained efficiently so as to satisfy objects of the experiment and to obtain adequate results. DOE allows systematic approach to calibration, and definition and evaluation of relationships between an experimental process and the resultant values thereof. Additionally, DOE provides various advisable effects. For example, DOE enables understanding of the vital few in variance of a parameter, provides a measurement for the effect of vital few upon response parameters, yields measured values and high-quality data more effectively as compared to One-Factor-At-a-Time calibration, permits measurement of uncertainty, minimizes test trials, and permits control of the nuisance variables. Such DOE include fractional factorial designs, full factorial designs, response surface methodology, mixture designs, Taguchi designs, or the like.

There is no particular limitation in the formulation of the composition for external skin application according to the present invention. The composition according to the present invention may be any skin adhesion type cosmetic formulation, such as lotion, skin toner, nourishing toner, nourishing cream, massage cream, pack, gel, essence, or the like. Also, the composition according to the present invention may be provided as a transdermal administration form such as lotion, ointment, gel, cream, a patch or a spraying agent. Additionally, each form of the composition for external skin application may further comprise other additives, as desired, according to the particular form and use of the composition.

Hereinafter, the present invention will be explained in more detail with reference to examples and experimental examples. However, the following examples are illustrative only, and the scope of the present invention is not limited thereto.

Mode for Invention

Experimental Example 1

Determination of PPAR-α Activation Capability Using One-Factor-At-A-Time (OFAT) Experiment The following test was carried out to determine PPAR-α activation capability.

CV-1 cells (ATCC CCL 70), i.e. monkey kidney epithelial cell line, were subcultured in a DMEM medium containing 10% bovine fetal serum treated with charcoal/dextrin. A phenol red-free medium was used to avoid the effect of estrogen upon phenol red. As plasmids, used were plasmids having PPRE (PPARs responsive element) as a promoter, followed by firefly luciferase genes as a reporter, the PPRE being activated by PPAR- (gene-containing PPAR- and ligand-bound PPAR-) bound next to the universal promoter expressed under general culture conditions, and a reference plasmid to which renilla luciferase genes were bound.

CV-1 cells were plated on a 24-well microtiter plate at a concentration of 5×10⁴ cells per well and cultured for 24 hours. Then, the above three types of plasmid genes were subjected to transient transfection by using a TransFast Kit available from Promega Co. After the cultured product was washed with PBS (phosphate buffered saline) once, the product was treated with a suitable concentration of sample materials, cultured again for 24 hours, and washed with PBS twice. Next, the cells were lysed with PLB (passive lysis buffer, Promega) once, and determined for luciferase activity by using a Dual-Luciferase Reporter Assay System Kit (Promega) in the samples and the controls. In this test, as a positive control, Wy14643 known as the strongest PPAR-α ligand was used. As negative controls, DMSO used to dissolve the samples and non-treated group were used. Each reported value was calculated as a ratio based on the negative control. The results are shown in the following Table 1, wherein each value is the mean value obtained after carrying out the test three times.

TABLE 1

Results for PPAR-γ activation analysis

| | PPAR-α Activation | |
|---|---|---|
| | 10 uM | 100 uM |
| (−) EGCG | 1.0 | 1.5 |
| (−) GCG | 1.1 | 2.3 |
| (−) ECG | 1.1 | 1.6 |
| (−) CG | 1.2 | 1.6 |
| (−) EGC | 1.3 | 1.0 |
| (−) GC | 1.1 | 1.0 |
| (−) EC | 1.2 | 1.2 |
| (+) EC | 1.3 | 1.2 |
| (−) CA | 1.4 | 1.2 |
| (+) CA | 1.5 | 1.4 |
| Gallic acid | 1.3 | 1.7 |
| Caffeine | 1.3 | 1.6 |
| Quercetin | 1.7 | 2.3 |
| Kaempferol | 1.7 | 1.4 |

TABLE 1-continued

Results for PPAR-γ activation analysis

| | PPAR-α Activation | | |
|---|---|---|---|
| | 10 uM | 100 uM | |
| Theobromine | 2.2 | 4.5 | |
| Theophylline | 1.4 | 1.7 | |
| Theanine | 1.8 | 1.9 | |
| Rutin hydrate | 1.6 | 1.3 | |
| Quinic acid | 1.3 | 1.7 | |
| Myricetin | 1.7 | 1.6 | |
| Negative control | 1.0 | 1.0 | |
| Positive Control | 0.1 uM | 1 uM | 10 uM |
| | 1.5 | 2.6 | 3.8 |

As can be seen from Table 1, among various components contained in green tea leave, gallocatechin gallate ((−)GCG), theobromine and quercetin show a similar degree effect of activating PPAR-α.

Experimental Example 2

Determination of PPAR-α Activation Capability Using Response Surface Methodology (RSM)

To optimize the PPAR-α activation capability of the components contained in green tea leaves, i.e. gallocatechin gallate, theobromine and quercetin, PPAR-α activation capability of which was determined in Experimental Example 1, response surface methodology (RSM) was used. When using RSM, it is possible to understand the level of an independent parameter where a response value is optimized, to estimate the effect of an independent parameter upon response parameters via estimation of a functional relationship between each independent parameter and dependent parameter, and to determine optimized experimental conditions. According to the present invention, central composite designs of RSM were carried out by using MiniTab 14. The results are shown in the following Table 2.

TABLE 2

Central Composite Designs and Measurements Thereof

| | C5 GCG | C6 theobromine | C7 quercetin | C8 StdOrder_1 | C9 RunOrder_1 | C10 Blocks_1 | C11 PtType_1 | C12 fold |
|---|---|---|---|---|---|---|---|---|
| 1 | 0 | 0 | 0 | 1 | 1 | 1 | 1 | 1.68624 |
| 2 | 100 | 0 | 0 | 2 | 2 | 1 | 1 | 1.19051 |
| 3 | 0 | 100 | 0 | 3 | 3 | 1 | 1 | 1.90453 |
| 4 | 100 | 100 | 0 | 4 | 4 | 1 | 1 | 2.55783 |
| 5 | 0 | 0 | 100 | 5 | 5 | 1 | 1 | 1.29966 |
| 6 | 100 | 0 | 100 | 6 | 6 | 1 | 1 | 2.02023 |
| 7 | 0 | 100 | 100 | 7 | 7 | 1 | 1 | 3.86848 |
| 8 | 100 | 100 | 100 | 8 | 8 | 1 | 1 | 4.05643 |
| 9 | 0 | 50 | 50 | 9 | 9 | 1 | 1 | 3.49402 |
| 10 | 135 | 50 | 50 | 10 | 10 | 1 | 1 | 4.65930 |
| 11 | 50 | 0 | 50 | 11 | 11 | 1 | 1 | 2.25292 |
| 12 | 50 | 135 | 50 | 12 | 12 | 1 | 1 | 4.05384 |
| 13 | 50 | 50 | 0 | 13 | 13 | 1 | 1 | 1.99345 |
| 14 | 50 | 50 | 135 | 14 | 14 | 1 | 1 | 4.16529 |
| 15 | 50 | 50 | 50 | 15 | 15 | 1 | 1 | 4.66230 |
| 16 | 50 | 50 | 50 | 16 | 16 | 1 | 1 | 3.53491 |
| 17 | 50 | 50 | 50 | 17 | 17 | 1 | 1 | 3.66028 |
| 18 | 50 | 50 | 50 | 18 | 18 | 1 | 1 | 3.56013 |
| 19 | 50 | 50 | 50 | 19 | 19 | 1 | 1 | 3.91237 |
| 20 | 50 | 50 | 50 | 20 | 20 | 1 | 1 | 2.99202 |

Then, an experiment was performed according to the above designs as shown in Table 2, and software analysis was carried out by using the values measured from the experiment.

Response Surface Regression: fold versus GCG, theobromine, quercetin
The analysis was done using coded units.

Estimated Regression Coefficients for fold

| Tera | Coef | SE Coef | T | P |
|---|---|---|---|---|
| Constant | 4.2440 | 0.2165 | 19.600 | 0.090 |
| GCG | 0.3420 | 0.2323 | 1.472 | 0.165 |
| theobromine | 0.8182 | 0.2738 | 2.988 | 0.010 |
| quercetin | 0.6292 | 0.2738 | 2.298 | 0.039 |
| theobromine*theobromine | −1.1066 | 0.3580 | −3.091 | 0.099 |
| quercetin*quercetin | −0.9463 | 0.3580 | −2.643 | 0.020 |
| theobromine*quercetin | 0.6651 | 0.3814 | 1.744 | 0.105 |

S = 0.5918 R-Sq = 60.7% R-Sq(adj) = 71.8%

Analysis of Variance for fold

| Source | CF | Seq SS | Adj SS | Ad. MS | T | P |
|---|---|---|---|---|---|---|
| Regression | 6 | 19.052 | 19.052 | 3.1753 | 9.07 | 0.001 |
| Linear | 3 | 11.367 | 5.078 | 1.6928 | 4.83 | 0.010 |
| Square | 2 | 6.619 | 6.619 | 3.3096 | 9.45 | 0.003 |
| Interaction | 1 | 1.065 | 1.065 | 1.0653 | 3.04 | 0.105 |
| Residual Error | 13 | 4.554 | 4.554 | 0.3503 | | |
| lack-of-Fit | 8 | 3.036 | 3.036 | 0.3295 | 1.25 | 0.420 |
| Pure Error | 5 | 1.517 | 1.517 | 0.3035 | | |
| Total | 19 | 23.605 | | | | |

Unusual Observations for fold

| Obs | StdOrder | fold | Fit | SE Fit | Residual | St Resid |
|---|---|---|---|---|---|---|
| ǀ 14 | 14 | 4.165 | 3.379 | 0.495 | 0.766 | 2.42 R |

R denotes an observation with a large standardized residual.

Figure 1:
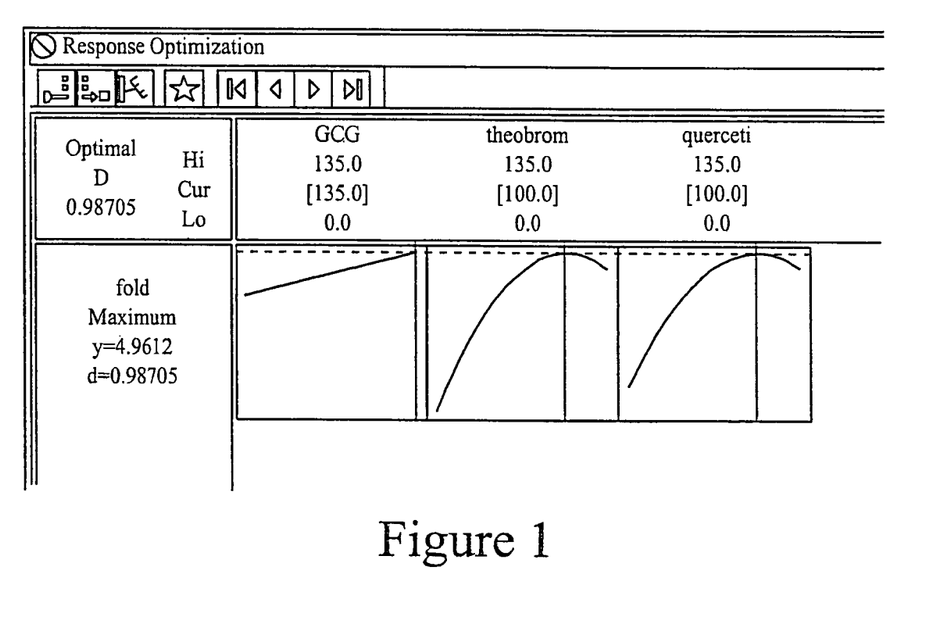
FIG. 1 is a graph illustrating how to select an optimal concentration by a response optimizer.
Figure 2A:
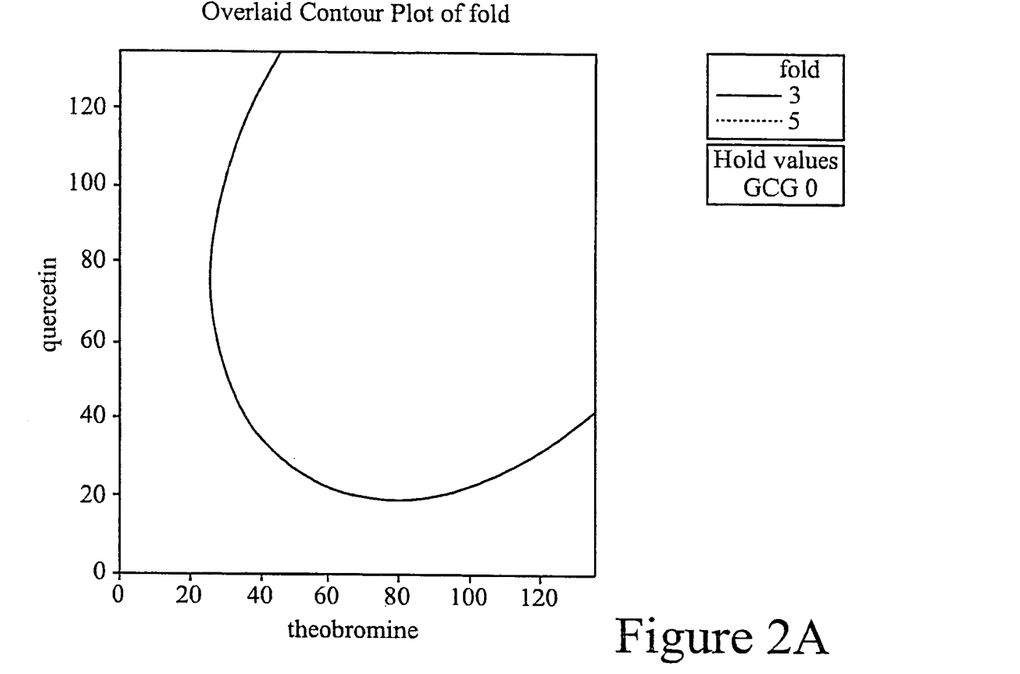
FIG. 2 is a graph illustration how to select an optimal concentration by using an overlaid contour plot.
Figure 2B:
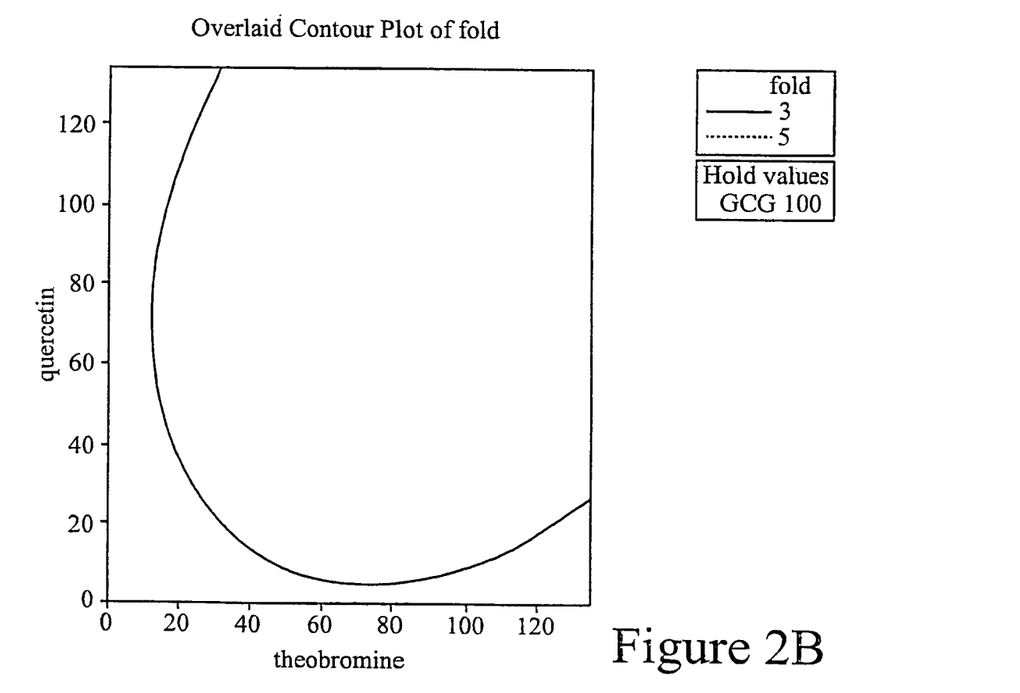
Figure 2C:
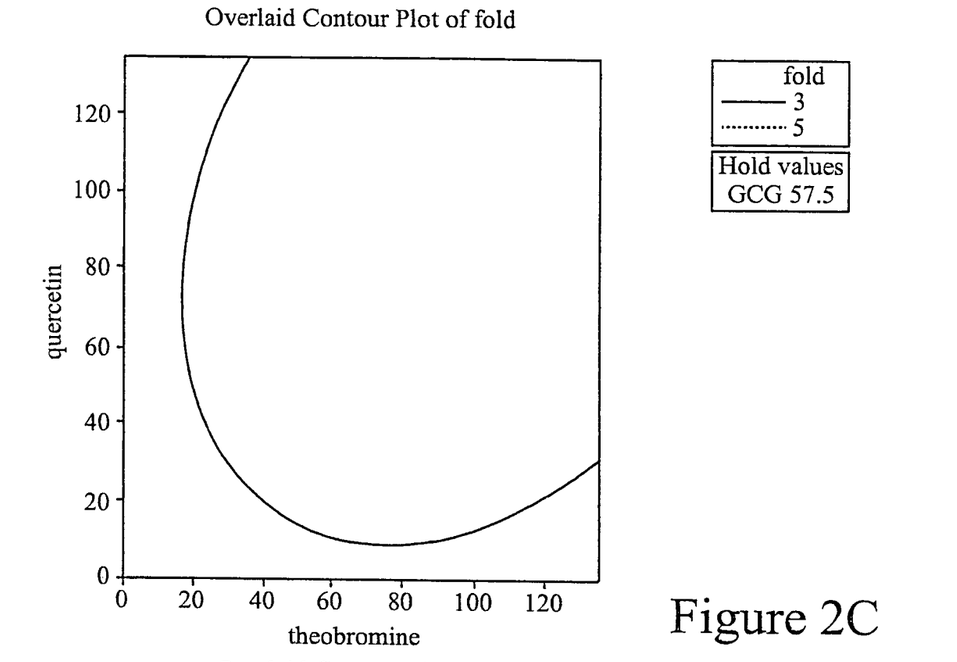
Figure 2D:
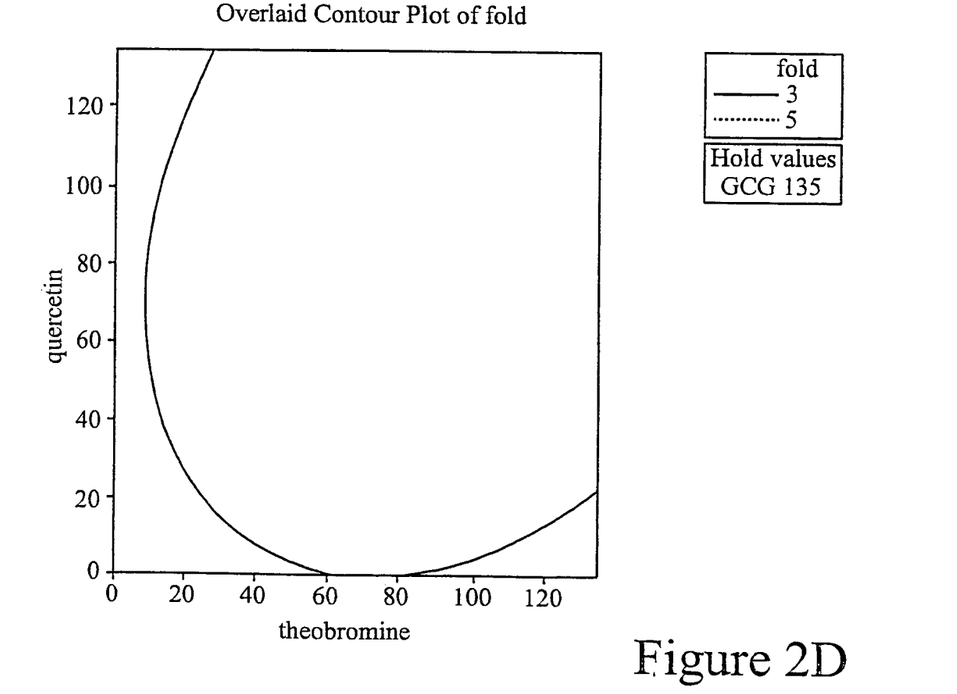

The results are shown in FIGS. 1 and 2 and the following Table 3.

TABLE 3

Optimized Concentration Ratio for PPAR-α Activation

| Component | Concentration Ratio | | |
|---|---|---|---|
| Gallocatechin gallate (GCG) | 0.7 or less | 0.7~1.4 | 1.4 or more |
| Theobromine | At least 0.4 | At least 0.3 | At least 0.2 |
| Quercetin | At least 0.4 | At least 0.3 | At least 0.2 |

As can be seen from the results of the software analysis, $R^2$=80.7% and $R^2$ (adj)=71.8%, which indicate a relatively high interrelation. Also, regression simulation shows similar results. Additionally, it is possible to recognize from the response optimizer as shown in FIG. 1 that the optimized concentration conditions showing the highest value according to the larger-the-better characteristics are accomplished at 135 μM of gallocatechin gallate, 100 μM of theobromine and 100 μM of quercetin. Further, it is possible to estimate optimal concentration ranges by using the overlaid contour plot as shown in FIG. 2. The results are shown in the above Table 3.

Example 3

Determination of Expression of Filaggrin Via RT-PCR Analysis

The cell line used in this example was a human keratinocyte HaCaT cell line distributed from Dr. Fusening in the German Cancer Research Center. The cells were pipetted into 60 mm dishes in a number of 1×10$^5$ cells per dish, cultured for one day, and treated with each test sample, followed by culturing for 24 hours. The test samples include a negative control (lanes 1 and 5), a mixture of gallocatechin gallate:theobromine:quercetin (130 μM:100 μM:100 μM) (lanes 2 and 6), and a mixture of gallocatechin gallate:theobromine:quercetin (65 μM:50 μM:50 μM) (lanes 3 and 7). The cells were cultured in a DMEM (Dulbeco's modified eagles medium, GibcoBRL, Life Technology) containing 10% fetal bovine serum (FBS) at 37° C. under 5% $CO_2$. The negative control was the cells cultured in the same medium in the absence of any test sample.

From the cells cultured and tested in the manner as described above, the total RNA was extracted by using trizol (Gibco Laboratories, USA), and RT-PCR (reverse transcriptional polymerase chain reaction) analysis was carried out according to the method provided by a one-step RNA PCR kit (AMV) (Takara Bio Inc., Japan). Herein, a primer for filaggrin (Bionia, Korea) was used as a primer for carrying out RT-PCR, and β-actin was used as an internal control to compare the expression in test samples with each other. The results are shown in FIG. 3.

Figure 3:
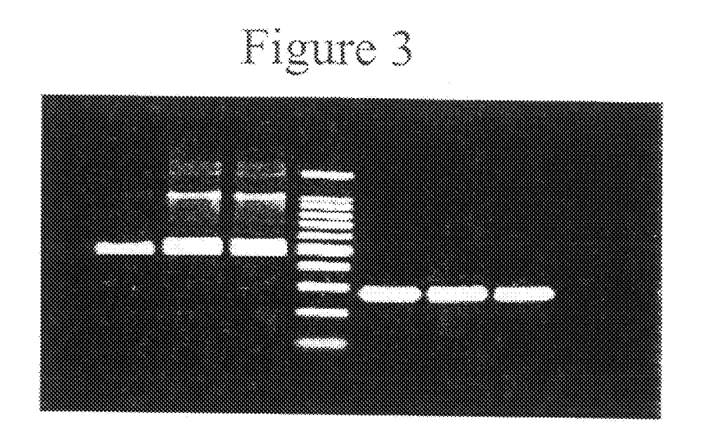
FIG. 3 is a view showing expression of filaggrin via RT-PCR analysis.

As can be seen from FIG. 3, a mixture containing gallocatechine gallate:theobromine:quercetin in a ratio of 130 μM:100 μM:100 μM (lane 2) and a mixture containing gallocatechine gallate:theobromine:quercetin in a ratio of 65 μM:50 μM:50 μM (lane 3) increase expression of filaggrin as compared to the non-treated group as a negative control (lane 1) by about 1.8~2.0 times (lane 1~3 represents filaggrin expression, lane 5~7 represents β-actin expression, and lane 4 is a 100 bp ladder as a marker). Therefore, it can be expected that a composition for external skin application comprising such mixtures shows skin-protecting and skin-moisturizing effects. Then, the following Experimental Example 4 was carried out.

Experimental Example 4

Determination of Skin Moisturizing Effect in Human Body

The skin toners of Examples 1~5 and Comparative Example 1 prepared according to the following Table 4 were determined for skin moisturizing effects.

Fifty men and women at their fifties to eighties showing a skin drying phenomenon were divided into five groups. Each group was allowed to use the skin toners of Examples 1~5 and Comparative Example 1 on their faces. Skin moisture content was measured before the application, 1 week, 2 weeks and 4 weeks after the application, and 2 weeks after the completion of the application (i.e. 6 weeks after the application) under constant temperature/constant humidity (24° C., relative humidity 40%) conditions by using a koniometer. The results are shown in the following Table 5. Each value listed in Table 5 is expressed as a percent ratio of an increase in the corresponding value measured after a predetermined period of time based on the value measured by the koniometer right before starting the test. The koniometer is a device for measuring skin moisture content by measuring electric conductivity on the epidermis.

Separately from the above test, each test panel was allowed to answer questions to perform subjective evaluation for the skin moisturizing effect simultaneously with instrumental evaluation. The results are shown in the following Table 6.

TABLE 4

| | Component (amount, wt %) | Ex. 1 | Ex. 2 | Ex. 3 | Ex. 4 | Ex. 5 | Comp. Ex. 1 |
|---|---|---|---|---|---|---|---|
| 1 | Purified water | 65.82 | 65.82 | 64.82 | 61.82 | 56.82 | 66.82 |
| 2 | Gallocatechin gallate | 1 | — | — | — | — | — |
| 3 | Mixture of gallocatechin gallate:theobromine:quercetin (1.3:1:1) | — | 1 | 2 | 5 | 10 | — |
| 4 | Vegetable cured oil | 1.50 | 1.50 | 1.50 | 1.50 | 1.50 | 1.50 |
| 5 | Stearic acid | 0.60 | 0.60 | 0.60 | 0.60 | 0.60 | 0.60 |
| 6 | Polygrlycerol-10 pentastearate & behenyl alcohol & sodium stearoyl lactylate | 1.00 | 1.00 | 1.00 | 1.00 | 1.00 | 1.00 |
| 7 | Arachidyl behenyl alcohol & arachydyl glucoside | 1.00 | 1.00 | 1.00 | 1.00 | 1.00 | 1.00 |
| 8 | Ceteraryl alcohol & cetearyl glucoside | 2.00 | 2.00 | 2.00 | 2.00 | 2.00 | 2.00 |
| 9 | PEG-100 stearate & glycerol oleate & propylene glycol | 1.50 | 1.50 | 1.50 | 1.50 | 1.50 | 1.50 |
| 10 | Caprylic/Capric triglyceride | 4.00 | 4.00 | 4.00 | 4.00 | 4.00 | 4.00 |
| 11 | Meadowfoam seed oil | 3.00 | 3.00 | 3.00 | 3.00 | 3.00 | 3.00 |
| 12 | Cetyl octanoate | 4.00 | 4.00 | 4.00 | 4.00 | 4.00 | 4.00 |
| 13 | Cyclomethicone | 6.00 | 6.00 | 6.00 | 6.00 | 6.00 | 6.00 |
| 14 | Methyl paraben | 0.20 | 0.20 | 0.20 | 0.20 | 0.20 | 0.20 |
| 15 | Propyl paraben | 0.10 | 0.10 | 0.10 | 0.10 | 0.10 | 0.10 |
| 16 | Disodium EDTA | 0.02 | 0.02 | 0.02 | 0.02 | 0.02 | 0.02 |
| 17 | Triethanol amine | 0.13 | 0.13 | 0.13 | 0.13 | 0.13 | 0.13 |
| 18 | Glycerin | 8.00 | 8.00 | 8.00 | 8.00 | 8.00 | 8.00 |
| 19 | Carbomer | 0.13 | 0.13 | 0.13 | 0.13 | 0.13 | 0.13 |

TABLE 5

Measurement of Moisture Content

| Test group | Moisture content increase (%) | | | |
|---|---|---|---|---|
| | After 1 week | After 2 weeks | After 4 weeks | After 6 weeks |
| Ex. 1 | 32 | 38 | 40 | 34 |
| Ex. 2 | 38 | 41 | 42 | 36 |
| Ex. 3 | 40 | 42 | 44 | 36 |
| Ex. 4 | 41 | 46 | 50 | 41 |
| Ex. 5 | 44 | 42 | 53 | 43 |
| Comp. Ex. 1 | 22 | 24 | 24 | 15 |

TABLE 6

Evaluation via Answer to Questions

| | Excellent | Good | Moderate | Poor |
|---|---|---|---|---|
| Ex. 1 | 1 | 5 | 3 | 1 |
| Ex. 2 | 2 | 4 | 3 | 1 |
| Ex. 3 | 2 | 6 | 2 | 0 |
| Ex. 4 | 3 | 6 | 1 | 0 |
| Ex. 5 | 4 | 4 | 2 | 0 |
| Comp. Ex. 1 | 1 | 1 | 5 | 3 |

As shown in Table 5, the test groups using the compositions of Examples 1~5 comprising gallocatechin, theobromine and quercetin show a significant increase in skin moisture content in a concentration-dependent manner, when compared to the test group using Comparative Example 1. Additionally, even 6 weeks after the application (2 weeks after the completion of the application), the skin moisture content is similar to the skin moisture content measured 1~2 weeks after the application. Thus, it can be seen that skin moisture content can be maintained to a certain degree without new application of the test material.

Also, as can be seen from the results of the examination listed in Table 6, the skin toners comprising the above mixture according to the present invention can improve skin drying conditions.

Experimental Example 5

Determination of Skin Barrier Effect Via Animal Test

The following test was carried out to determine the effect of the composition according to the present invention upon recovery of skin barriers on the skin damaged for a long period of time. Acetone was applied onto the backs of 8~10 week-aged young hairless rats in a periodic manner twice per day for 5 days, so that the back skin of the test animals was damaged in terms of skin barrier functions. Then, TEWL (transepidermal water loss) was measured by using an evaporimeter to select test animals showing a TEWL of 40 $g/m^2/hr$ or more. To the selected test animals, vehicle (propylene glycol:ethanol=7:3) and the test materials comprising the compositions of Examples 6 and 7 and Comparative Examples 2 and 3 as shown in the following Table 7 were applied continuously in a dose of 200 μl per 5 $cm^2$ of skin area twice per day for 3 days. During the application, TEWL was measured at predetermined intervals, and a skin barrier recovery ratio was calculated according to the following Mathematical Formula 1. The results are shown in the following Table 7.

$$\text{Skin barrier recovery ratio}(\%) = (TEWL_0 - TEWL_X)/(TEWL_0 - TEWL_{basal}) \times 100 \quad \text{[Mathematical Formula 1]}$$

$TEWL_0$: TEWL measured right after skin damage $TEWL_X$: TEWL measured after a predetermined of time $TEWL_{basal}$: initial TEWL value

TABLE 7

| | Skin Barrier Recovery Ratio(%) | | | | |
|---|---|---|---|---|---|
| Item | Test Sample | 0 hr | 3 hr | 6 hr | 30 hr |
| Comp. Ex. 2 | Control (PG:EtOH = 7:3) | 0 | 25 | 34 | 74 |
| Comp. Ex. 3 | Epigallocatechin gallate (EGCG) 1% | 0 | 42 | 50 | 79 |
| Ex. 6 | Gallocatechin gallate (GCG) 1% | 0 | 46 | 53 | 84 |
| Ex. 7 | Gallocatechin gallate: theobromine:quercetin (1.3:1:1) mixture 1% | 0 | 33 | 55 | 96 |

As shown in Table 7, the test groups treated with gallocatechin gallate (Example 6) or with a mixture of gallocatechin gallate:theobromine:quercetin (Example 7) provide a higher skin barrier recovery ratio into normal skin conditions, when compared to the controls (Comparative Examples 2 and 3). In addition to such excellent recovery of the skin barrier, Examples 6 and 7 show a significant increase in skin moisture content. Thus, it can be seen that the composition according to the present invention provides an excellent skin moisturizing effect.

Figure 4:
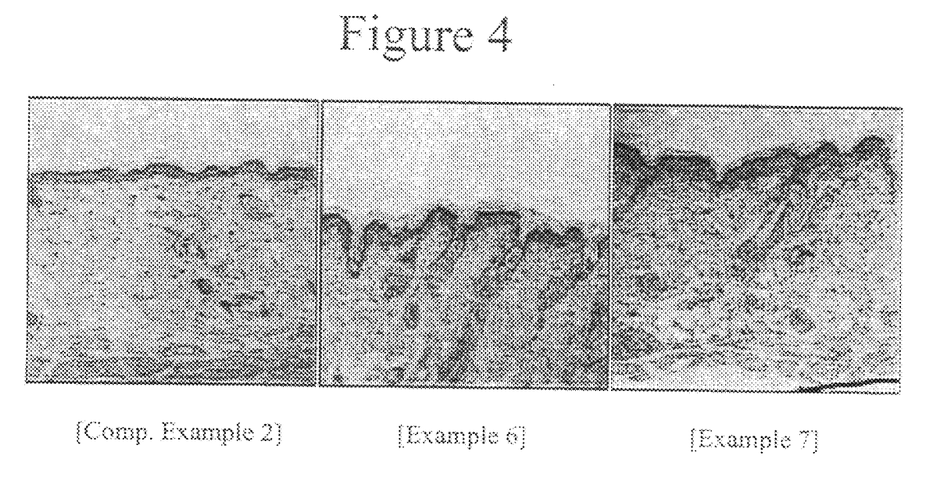
FIG. 4 is a photographic view showing the epidermal layers observed by carrying out immunohistochemical staining using involucrin antibodies.

Additionally, a piece of skin tissue was cut from the test animals, fixed with paraffin, and was subjected to immunohistochemical staining by using involucrin (INV) antibodies, while observing variations in the epidermal layers. The results are shown in FIG. 4. Involucrin was observed as the part stained with a brown color.

As can be seen from FIG. 4, the test groups to which gallocatechin gallate (Example 6) or a mixture of gallocatechin:theobromine:quercetin (Example 7) was applied show an increase in involucrin expression as compared to the control (Comparative Example 2). This indicates that the composition according to the present invention can provide an excellent effect of improving damaged skin barriers.

INDUSTRIAL APPLICABILITY

The composition for external skin application having a skin moisturizing effect according to the present invention comprises gallocatechin gallate contained in green tea leaves to control the activity of PPAR-α. The composition according to the present invention may further comprise theobromine and quercetin at an optimized ratio to provide an enhanced skin moisturizing effect and anti-drying effect.

The invention claimed is:

1. A method of moisturizing the skin comprising topically applying to the skin a skin moisturizing composition consisting of gallocatechin gallate, theobromine and quercetin as active ingredients.

2. The method according to claim 1, wherein each active ingredient in the composition is used in the following molar concentration: at least 0.3 moles of theobromine and at least 0.3 moles of quercetin in combination with 0.7~1.4 moles or less of gallocatechin gallate (GCG).

3. The method according to claim 1, wherein each active ingredient in the composition is used in the following molar concentration: at least 0.2 moles of theobromine and at least 0.2 moles of quercetin in combination with 1.4 moles or more of gallocatechin gallate (GCG).

4. The method according to claim 1, wherein each active ingredient in the composition is used in an amount of 0.001~30.0 wt % based on the total weight of the composition.

5. The method according to claim 1, which activates peroxisome proliferator activated receptor isoform alpha (PPAR-α).

6. The method according to claim 1, which stimulates expression of filaggrin on the skin.

7. The method according to claim 1, which stimulates expression of involucrin on the skin.

8. A method of moisturizing the skin comprising topically applying to the skin a skin moisturizing composition consisting of 0.7 moles or less of gallocatechin gallate (GCG), at least 0.4 moles of theobromine and at least 0.4 moles of quercetin as active ingredients.

* * * * *